(12) United States Patent
Sammler et al.

(10) Patent No.: US 6,544,216 B1
(45) Date of Patent: Apr. 8, 2003

(54) INTRACARDIAC BLOOD PUMP

(75) Inventors: Rolf Sammler, Luedinghausen (DE); Thorsten Siess, Wuerselen (DE); Christoph Nix, Aachen (DE); Max Eisen, Aachen (DE); Jens Peter Hutzenlaub, Aachen (DE); Bart Meyns, Leuven (BE)

(73) Assignee: Impella Cardiotechnik Aktiengesellschaft (DE)

( * ) Notice: Subject to any disclaimer, the term of this patent is extended or adjusted under 35 U.S.C. 154(b) by 0 days.

(21) Appl. No.: 09/446,770
(22) PCT Filed: Apr. 24, 1999
(86) PCT No.: PCT/EP99/02790
§ 371 (c)(1), (2), (4) Date: May 30, 2000
(87) PCT Pub. No.: WO99/58170
PCT Pub. Date: Nov. 18, 1999

(30) Foreign Application Priority Data

May 13, 1998 (DE) .......................................... 198 21 307

(51) Int. Cl.⁷ .............................................. A61M 29/00
(52) U.S. Cl. ................................................... 604/95.03
(58) Field of Search ...................... 604/96.01, 101.01, 604/101.04, 102.01, 103, 523, 532, 530, 912, 920, 95.03, 95.01; 606/194

(56) References Cited

U.S. PATENT DOCUMENTS

| 3,995,623 A | 12/1976 | Blake et al. ............. 604/9.5 X |
| 5,584,803 A | * 12/1996 | Stevens et al. ..... 604/101.01 X |
| 5,882,334 A | * 3/1999 | Sepetka et al. ........ 604/164.08 |

FOREIGN PATENT DOCUMENTS

| DE | 196 22 335 A1 | 4/1996 |
| DE | 298 04 046 UI | 4/1998 |
| WO | WO 94/09835 | 10/1993 |

OTHER PUBLICATIONS

Article In Vitro and In Vivo Assessment of an Intravenous Axial Flow Pump for Right Heart Assist, from the National Cardiovascular Center Research Insittute, Osaka Japan, Jul.–Sep. 1994 Issue No. 3.

* cited by examiner

Primary Examiner—Anhtuan T. Nguyen
(74) Attorney, Agent, or Firm—Fulwider Patton Lee & Utecht, LLP

(57) ABSTRACT

The intracardiac blood pump (10) comprises a drive section (11) and a pump section (12). A flexible pump hose (14) is connected to the pump section (12). To lay the pump hose (14) from the right atrium (21) to the pulmonary artery (26) the distal end of the pump hose (14) comprises a balloon (35) which acts as guide element in the blood flow and is entrained by the natural blood flow. This facilitates placing of the blood pump in the heart.

13 Claims, 3 Drawing Sheets

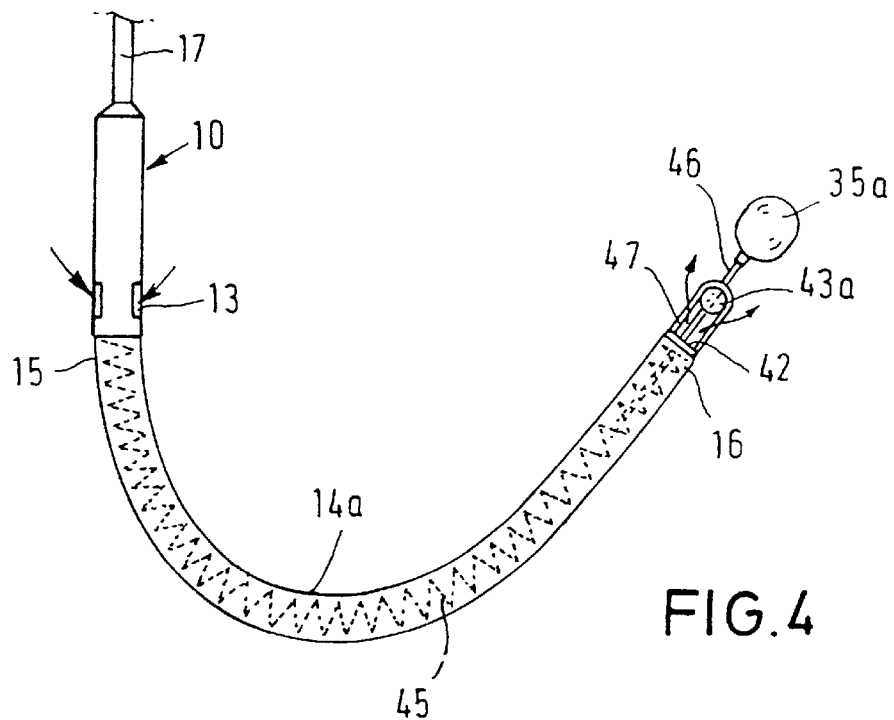
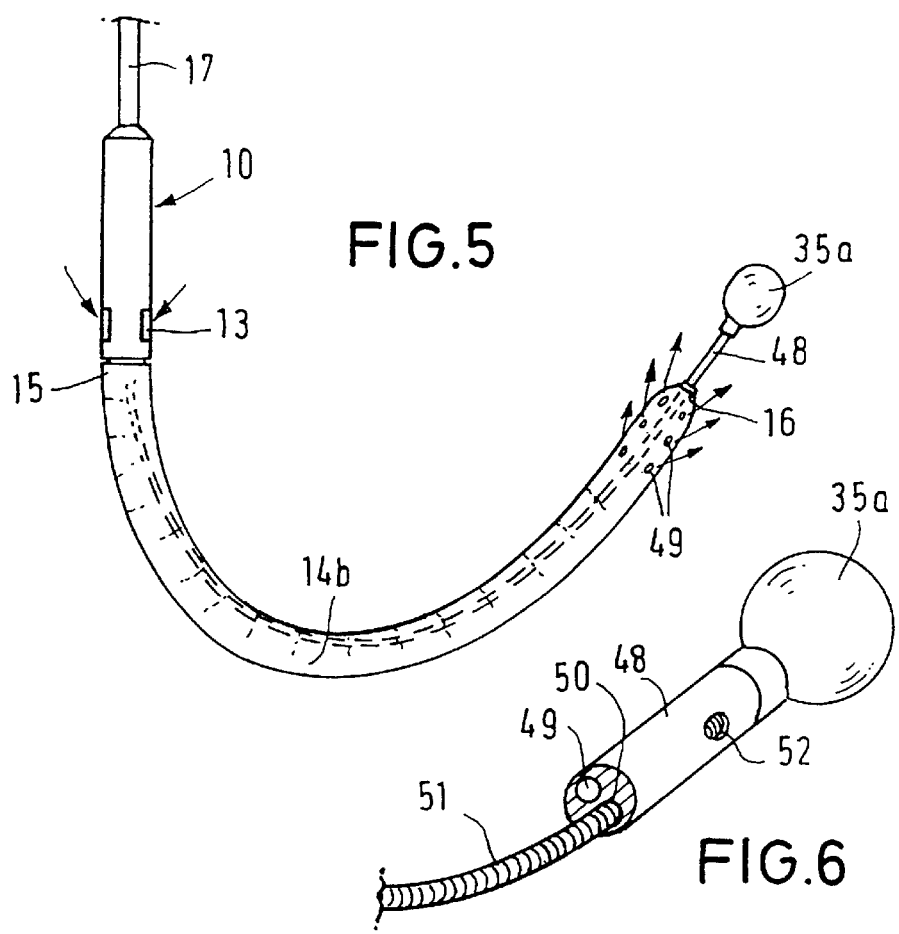

INTRACARDIAC BLOOD PUMP

The invention relates to an intracardiac blood pump and in particular to a blood pump which can be completely inserted through adjacent vessels into the heart to support the natural pumping function of the heart or replace it by continuous pumping operation.

A pump device for supporting the heart function is described in WO94/09835 (Jarvik). Said pump device comprises pumps operating independently of each other, each pump being provided with a pump section and a drive section rigidly connected with the pump device. The pump section of the one pump is inserted through an apecal operation opening into the left ventricle such that it delivers from the left ventrical into the aorta. The other pump section is inserted through another preferably apecal operation opening into the right-ventricle so that it delivers from the right atrium into the pulmonary artery. Each of the pumps is extended at its pump outlet by a hose-type outlet canula which may be guided through the respective heart valve.

An intracardiac blood pump which is inserted from the aorta through the aortic valve into the left ventricle is known from WO97/37696 (Rau et al). Here the pump inlet is extended by a hose passing through the aortic valve.

From WO97/37697 (Rau et al.) an intravascular blood pump is known which can moved through a blood vessel. This blood pump, too, is, extended at its outlet end by an intake hose. Said intake hose comprises an inflatable balloon serving as isolating device and preventing blood from flowing laterally along the outside of the intake hose.

Finally, U.S. Pat. No. 4,753,221 (Kensey et al.) describes a pump catheter having a pump to be placed in the heart. Said pump comprises an impeller and a pump casing surrounding said impeller. The pump casing can be placed in the heart when the former is in the collapsed condition and subsequently unfolded by inflating a balloon connected with the pump casing.

Further, small-lumen catheters for pressure and volumetric flow measurement are known which serve for diagnostic purposes and comprise an inflatable balloon at the distal catheter end. Said balloon is used for positioning the catheter tip in the pulmonary artery.

Intracardiac blood pumps which are inserted through a blood vessel into the heart are difficult to correctly place in the heart. In particular when the blood pump is inserted through the upper vena cava to pump blood from the right atrium into the pulmonary artery, correct placing of the blood pump is difficult since the pump must perform a bend of approximately 180° to ensure that the intake opening is located in the right atrium and the outlet opening in the pulmonary artery. Further, numerous fibres and tendines exist in the right ventricle, which retain the tricuspid valve, protect the leaflet of the valve against bulging inside out and ensure inherent stability of the heart. A blood pump inserted through a vena cava must be guided between such fibres and tendines.

It is the object of the invention to provide an intracardiac blood pump which can be relatively easily placed in the heart.

According to the invention this object is solved by means of the features stated in claim 1.

A flexible hose is attached to the pump outlet of the blood pump according to the invention with the distal end of the hose comprising a balloon acting as guide element in the blood flow. The invention utilizes the fact that the blood naturally flows in the heart from the vena cava into the right atrium and through the right ventricle into the pulmonary artery. The blood pump which comprises a balloon at the distal end of the hose is inserted along this path with the balloon floating in the blood flow automatically finds its way from the right atrium into the pulmonary artery. The hose outlet is subsequently stabilized in the pulmonary artery wheras the pump section is positioned in the right atrium. The pump hose performs a bend of approximately 180°. In this way it is possible to correctly place the blood pump including the pump hose in the heart without the hose outlet pushing against the ventricular septa or diagnostic aids (X-rays or ultrasound) being required.

The term intracardiac within the meaning of the present invention includes the heart chambers (ventricles), the atria and the adjacent vascular stumps.

The pump hose should prefably be prebent according to its final position which it will assume in the heart. This requires bending by at least approximately 150°. Although the pump hose must be capable of being elongated for insertion through the vena cava it should assume a U-form or a V-form in the slackened condition. It would be particularly preferred that the pump hose displays a flexural rigidity which decreases from the proximal end to the distal end. In this way the distal end as path finder can be easily moved so that the balloon can better follow the natural blood flow.

The balloon must not necessarily be directly attached to the pump hose. It may also be fixed to a catheter which forms part of the pump hose and extends on the inside or the outside of the latter. In any case a lumen must extend towards the balloon via which the balloon can be inflated. A second lumen may additionally be provided into which a guide wire is inserted which facilitates advancing of the pump hose through the vascular system. After removal of the guide wire said second lumen may be used as pressure measuring lumen.

According to a preferred embodiment the balloon is configured as annular balloon and surrounds the pump hose. The advantage of such a configuration is that owing to the presence of the balloon the distal hose end has an increased outside diameter and is thus retained by the pulmonary valve. In this way the balloon helps to anchor the hose end to the pulmonary valve while the hose outlet is located in the pulmonary artery. This prevents the hose outlet from slipping out the pulmonary artery. Another advantage is that the annular balloon forms a rounded blunt end of the pump hose so that the pump hose cannot damage the vascular or heart walls or other parts of the heart. Finally, the hose end is prevented from hooking at the valve margin or tendines in the heart.

Since the pump section pumps into the pump hose, the pump hose is automatically kept open. Thus a collapsible hose can be used as pump hose, e. g. a hose made of sheet material, whose wall is not inherently stable. Through this hose a catheter may extend to the balloon arranged at the distal end.

When an intracardiac blood pump with a flexible pump hose is used there is the danger that the blood leaving the hose outlet causes a recoil at the hose, which may result in a retrograde displacement of the hose. Thus the hose may slip out of the pulmonary valve. It is thus a further object of the invention to provide an intracardiac blood pump in which displacements of the hose due to hydraulic reaction forces are prevented.

According to the invention this object is solved by means of the features stated in claim 13. To the distal end of the hose a traction element is fixed to which the pumped flow is directed. Said traction element may be a leaflet or a balloon. The blood flow leaving the hose end pushes against the traction element, which produces a forward directed force acting against the retraction force of the hose. In this way the traction element serves for a stabilized positioning of the pump hose.

Hereinafter embodiments of the invention are explained in detail with reference to the drawings in which:

FIG. 4 shows a second embodiment of the blood pump,

FIG. 5 shows a third embodiment and

FIG. 6 shows on an enlarged scale a representation of the catheter of the embodiment shown in FIG. 5.

Figure 1:
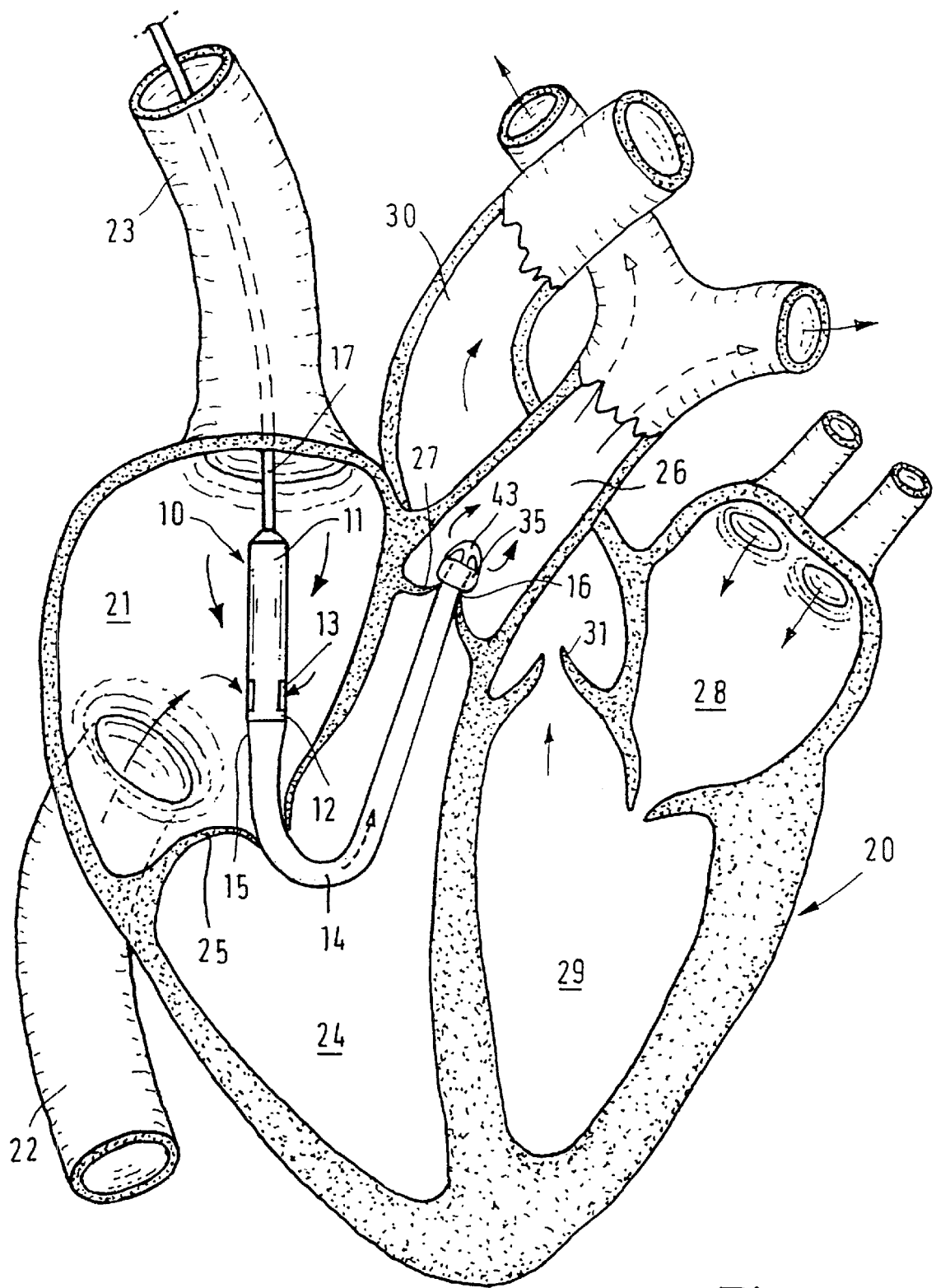
FIG. 1 shows a cross-section of the heart with a blood pump arranged therein.

According to FIG. 1 the blood pump 10 is an intravascular blood pump, i. e. a blood pump which can be inserted through the blood vessel system of a patient into the heart. The outside diameter of such a blood pump is at no place larger than 8 mm. The pump 10 comprises a drive section 11 and a pump section 12 rigidly connected with the drive section. The pump corresponds e. g. to that described in WO97/37696 so its internal structure needs not be explained here in detail. In the transition area between drive section 11 and pump section 12 intake openings 13 are arranged through which blood is radially taken in from outside. The pump section 12 comprises an impeller (not shown) which moves the blood in axial direction. To the outlet of the pump section 12 a pump hose 14 is connected. Said pump hose comprises a proximal end 15 connected with the pump outlet and a distal end 16 forming the hose outlet.

The proximal end of the pump 10 is connected with a catheter 17 which also contains the electrical supply lines for the drive section 11. Further, the catheter 17 comprises a lumen which can be connected to a compressed air source.

The pump hose 14 and the catheter 17 are of flexible design. The rigid length of the pump 10 does not exceed 35 mm to allow the pump to move through the bends of the blood vessel system. The length of the pump hose 14 is at least twice that of the rigid length of the pump. The pump hose is approximately 12 cm long and has an outside diameter of approximately 8 mm. Its wall thickness is 0.05 mm to 0.2 mm. The bending radius of the hose bend is 40 mm to 60 mm.

FIG. 1 shows a cross-section of the heart 20. The lower vena cava 22 and the upper vena cava 23 end in the right atrium 21. Between the right atrium 21 and the right ventricle 24 the tricuspid valve 25 is located. Between the right ventricle 24 and the pulmonary artery 26 the pulmonary valve 27 is located. The blood flows from the pulmonary artery 26 to the lung and from there back to the left atrium 28 and the left ventricle 29. Between the left ventricle 29 and the aorta 30 the aortic valve 31 is located.

The pump 10 is positioned as right ventricular pump such that it delivers from the right atrium 21 into the pulmonary artery 26. For this purpose it is, in the embodiment shown, placed through the upper vena cava 23. It would also be possible to place it through the lower vena cava 22. During insertion of the pump 10 the pump hose 14 of the pump lies ahead, i. e. it is positioned downstream of the pump 10 as seen in the direction of flow of the blood surrounding the pump.

Figure 2:
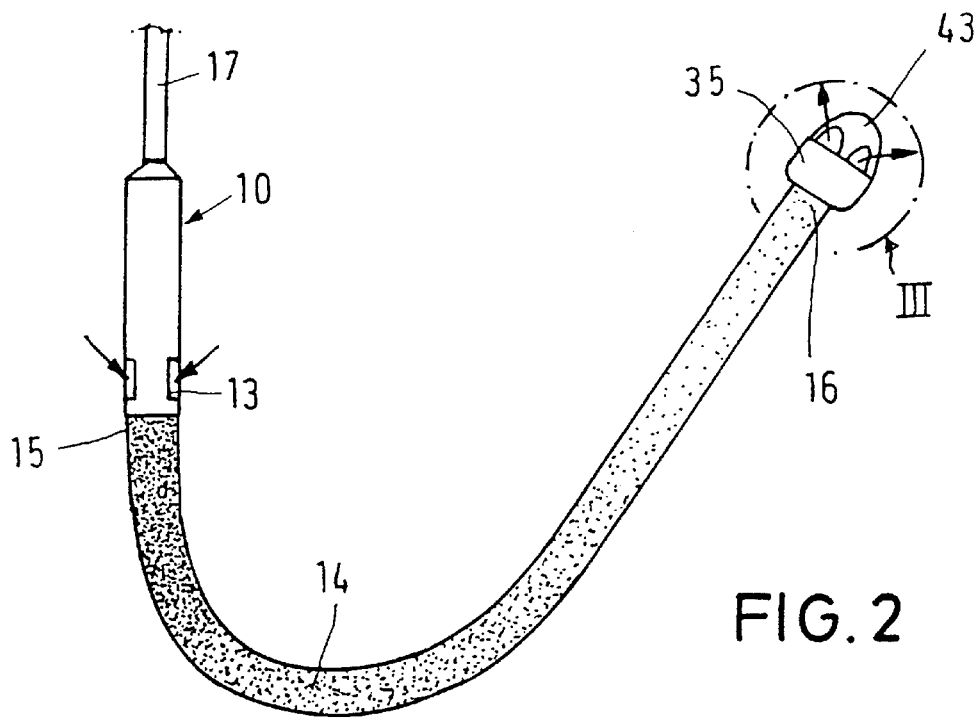
FIG. 2 shows a representation of the blood pump of FIG. 1.
Figure 3:
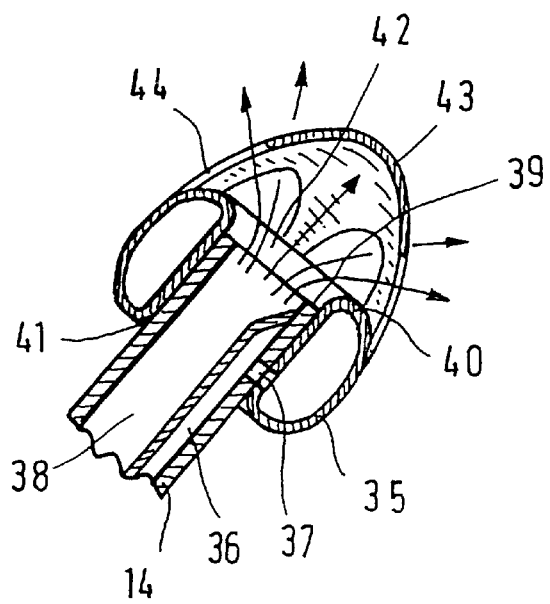
FIG. 3 shows a section of detail III of FIG. 2.

At the distal end 16 of the pump hose 14 a balloon 35 is arranged which is configured here as annular balloon as shown in FIG. 2 and FIG. 3. The balloon 35 filled with gas (e. g. air, helium, $CO_2$) or a liquid has a larger outside diameter than the pump hose 14. Consequently, the balloon 35 acts as a guide element entrained by the natural blood flow. Thus the balloon 35 is washed via the natural blood path first into the right ventricle 24 and then into the pulmonary atery 26.

The balloon 35 is inflated by a pressure being produced in a pressure lumen 36 of the pump hose 14. The pressure lumen 36 is connected via openings 37 with the inside of the annular balloon 35. In the pump hose 14 the blood flows through the blood lumen 38 whose cross-section is considerably larger than that of the pressure lumen 36. The pressure lumen 36 is connected to a corresponding pressure lumen of the proximal catheter 17 so that its pressure can be extracorporeally controlled.

The pump hose 14 is shown in FIG. 2 in slackened condition. The pump hose is prebent into U-form or V-form, i. e. it can remember the form so that it is not subjected to any essential constraint in the heart and, in turn, does not exert any essential constraint on the heart as shown in FIG. 1. In FIG. 2 the blackened dotted area indicates the rigidity of the pump hose 14. At the proximal end 15 said rigidity is very large and continuously decreases towards the distal end 16. This means that the distal end 16 where the balloon 35 is arranged can be freely moved and guided by the balloon.

As can be seen from FIG. 3, the distal end of the balloon 35 projects beyond the end 39 of the pump hose 14 so that the balloon 35 forms a rounded hose end 40 which does not run the risk of hooking at obstacles. At the proximal end of the balloon 35 an annular undercut 41 is formed into which the tips of the pulmonary valve 27 can penetrate as is shown in FIG. 1 so that the pulmonary valve prevents the hose end from receding.

As is shown in FIGS. 2 and 3 a traction element 43 traverses the hose outlet 42 in the form of a dome-shaped leaflet. Said traction element 43 comprises a thin and flexible membrane which is fixed to the balloon 35 by means of webs 44. The blood flowing out of the hose outlet 42 flows against the traction element 43 thus exerting a tractive force onto the pump hose 14 which counteracts the recoil effect. This prevents the distal end 16 of the pump hose from displacing and possibly slipping out of the pulmonary valve 27 due to the hydraulic recoil.

The pump hose 14 is preferably made of polyurethane which has turned out to be particulary suitable.

In the embodiment shown in FIG. 4 a pump hose 14a is connected to the pump 10, which comprises an elastic supporting structure 45 in the form of a carbon or metal spiral. Said supporting structure 45 keeps the pump hose open and effects the desired flexural rigidity which may vary over the hose length. A catheter 46 extends through the pump hose 45, which is provided with a balloon 35a at its distal end. Said balloon acts as guide element for the pump hose 14a. The catheter 46 contains a pressure lumen. Its outside diameter is considerably smaller than the diameter of the pump hose 14a so that an adequate cross-section for the blood flow is available in the pump hose. The catheter 46 is connected with the catheter 17.

A ball as traction element 43a is arranged at a distance behind the hose outlet 42 and fixed to the catheter 46. The blood flow pushing against the traction element 43a prevents the distal hose end 16 from receding towards the pump. 10. The pump hose 14a is anchored to the traction element 43a by means of a holding fixture 47.

In the embodiment shown in FIGS. 5 and 6 the pump hose 14a is a collapsible pump hose made of thin sheet material with no inherent stability. A catheter 48 comprising a balloon 35a at its distal end extends through the pump hose 14b. Said catheter 48 is connected with catheter 17. The distal end 16 of the pump hose 14b is connected with the catheter 48 and the pump hose 14b comprises outlet openings 49 through which the blood flows out. When the pump is inserted as shown in FIG. 5 the pump is out of operation so that the pump hose 14b is collapsed. With the aid of the balloon 35a the soft and flexible catheter 48 is placed in the heart thus positioning the pump hose 14b. If the pump is subsequently placed into operation, the pump hose 14b is expanded.

To facilitate the placing process the catheter 36,36,48 shown in FIG. 6 may contain, in addition to the pressure lumen 49 leading to the balloon 35a, another lumen 50 destined for accommodation of a guide wire 51 and, after removal of the guide wire, for external pressure measurement. Said guide wire 51 which also extends through the catheter 17 and the pump 10 allows the operating surgeon to controllably influence the laying of the pump hose. Following that the guide wire 51 is removed.

According to FIG. 6 an opening 52 may be provided in the catheter 48, which is connected with the lumen 50 and blocked by the guide wire 51. When the guide wire 51 has been removed from the lumen 50, blood enters the lumen 50 through the opening 52. The lumen 50 can be connected with a blood pressure instrument so that the blood pressure in the pulmonary artery can be measured and influenced, if necessary, during the pumping process.

If placing of the pump hose is effected without a guide wire, the pressure can be measured at the place 52 in the lumen 50 with the aid of measurable pressure profiles. On the basis of the pressure profiles the exact position of the distal pump hose tip can thus be determined.

The diameter of the balloon may not be so large that it essentially impedes the flow through the pulmonary artery 26 or even isolates the pulmonary artery. As a rule, the diameter may not exceed 30 mm. Further, in contrast to a dilating balloon, the balloon should display a high elasticity. Silicone, latex and preferably polyurethane are suitable balloon materials owing to their elasticity properties.

While floating in the blood flow as guide element for the catheter hose, the balloon may be strongly inflated at high pressure and subsequently decreased in size by reducing the pressure in order to act as traction element to which the pumped flow is directed.

What is claimed is:

1. An intracardiac blood pump, comprising:
   a pump section having a distal end and a proximal end, dimensioned for receipt within a blood lumen and configured for radially intaking and axially discharging blood;
   a catheter connected to said pump section's proximal end;
   a pump hose connected to said pump section's distal end for conducting blood discharged from said pump section therethrough to an outlet formed on its distal end; and
   a balloon disposed adjacent to the distal end of said pump hose and capable of being entrained by blood flow so as to act as a guide element.

2. The intracardiac of claim 1, wherein the pump hose is prebent by more than 100°, preferably by approximately 150°.

3. The intracardiac blood pump of claim 1, wherein the pump hose displays flexural rigidity which decreases from its proximal end to its distal end.

4. The intracardiac blood pump of claim 1, wherein the pump hose has a catheter disposed on its inside or its outside which projects beyond the distal end of the pump hose and comprises the balloon beyond the distal end.

5. The intracardiac blood pump of claim 1, wherein the balloon is configured as an annular balloon that surrounds the pump hose.

6. The intracardiac blood pump of claim 5, wherein the annular balloon forms a rounded hose tip.

7. The intracardiac blood pump of claim 1, wherein the pump hose is collapsible.

8. The intracardiac blood pump of claim 1, wherein the pump hose contains an elastic supporting structure.

9. The intracardiac blood pump of claim 1, wherein the pump hose comprises a catheter capable of having a guide wire inserted there into.

10. The intracardiac blood pump of claim 1, wherein the catheter comprises a lumen for receiving a guide wire and a pressure lumen.

11. The intracardiac blood pump of claim 1, wherein the catheter comprises a lumen usable as a pressure measuring lumen.

12. The intracardiac blood pump of claim 1, wherein the diameter of the balloon in an inflated condition does not exceed 30 mm.

13. An intracardiac blood pump, comprising:
   a pump section having a distal end and a proximal end, dimensioned for receipt within a blood lumen and configured for radially intaking and axially discharging blood;
   a catheter connected to said pump section's proximal end;
   a pump hose connected to said pump section's distal end for conducting blood discharged from said pump section therethrough to an outlet formed on its distal end; and
   a traction element, affixed to the distal end of the pump hose so as to receive blood flowing from said hose outlet.

* * * * *